(12) United States Patent
Renucci et al.

(10) Patent No.: US 9,333,153 B1
(45) Date of Patent: May 10, 2016

(54) MULTI-FUNCTIONAL MALE SHAVING PRODUCT

(71) Applicant: Renuskin, LLC, Grand Rapids, MI (US)

(72) Inventors: John Renucci, Grand Rapids, MI (US); Susan Goldsberry, Fountain Valley, CA (US); Lyndon Garcines, Fountain Valley, CA (US)

(73) Assignee: Renuskin, LLC, Grand Rapids, MI (US)

( * ) Notice: Subject to any disclaimer, the term of this patent is extended or adjusted under 35 U.S.C. 154(b) by 0 days.

(21) Appl. No.: 14/224,693

(22) Filed: Mar. 25, 2014

(51) Int. Cl.
| | | |
|---|---|---|
| *A61K 8/19* | (2006.01) | |
| *A61Q 9/00* | (2006.01) | |
| *A61K 8/04* | (2006.01) | |
| *A61Q 9/02* | (2006.01) | |
| *A61Q 19/08* | (2006.01) | |

(52) U.S. Cl.
CPC . *A61K 8/046* (2013.01); *A61Q 9/02* (2013.01); *A61Q 19/08* (2013.01)

(58) Field of Classification Search
CPC ....... A61K 8/046; A61K 8/361; A61K 8/466; A61K 8/00; A61K 8/975; A61K 8/315; A61Q 9/02

See application file for complete search history.

(56) References Cited

U.S. PATENT DOCUMENTS

| 5,976,520 | A  | * | 11/1999 | Babinski et al. | 424/73 |
| 2004/0136916 | A1 | * | 7/2004 | Garrison | 424/45 |
| 2009/0017147 | A1 | * | 1/2009 | Lintner et al. | 424/780 |
| 2010/0311667 | A1 | * | 12/2010 | Hocquaux et al. | 514/18.8 |

* cited by examiner

*Primary Examiner* — Anoop Singh
*Assistant Examiner* — Doan Phan
(74) *Attorney, Agent, or Firm* — Louis C. Paul

(57) ABSTRACT

A multi-functional, foaming male shaving product comprising of (i) a surfactant blend consisting of an alkyl isethionate and a glyceryl alkanoate, wherein the ratio, by weight of alkyl isethionate to glyceryl alkanoate is between 5:1 to 8:1, (ii) a copolymer of acrylamide and iallyldimethylammonium chloride; (iii) a combination of a yeast extract, an algae extract, an extract of *Chondrus crispus*, and glucosamine hydrochloride; and (iv) a continuous self-foaming agent containing a volatile hydrofluoroether.

7 Claims, No Drawings

MULTI-FUNCTIONAL MALE SHAVING PRODUCT

FIELD OF THE INVENTION

The present invention relates to a multi-functional male shaving product that with repeated uses produces visible anti-aging benefits.

BACKGROUND OF THE INVENTION

For decades, men's skincare regimens were limited, involving separate steps of washing/cleansing and shaving. With increasing awareness of the damaging effects of exposure to ultraviolet radiation, this simple two-part regimen expanded, with more men using sunscreens.

With the aging of both the baby-boom generation and Generation X, men, like women, are increasingly concerned about maintaining a younger looking appearance. This is captured in comments made by NPD Group, a leading market research firm, in August 2012 when releasing its most recent report on continued growth in the $45.5 million men's skin care market: "Many men are catching up to women with embracing the routine of a facial skin care regimen." http://www.gcimagazine.com/marketstrends/segments/skincare/167319105.html.

However, men's skin physiology and grooming habits, differ significantly from women. For example, men typically have thicker skin with smaller pores than women, making it more difficult for treatment products to penetrate. Moreover, because men shave regularly, the skin's protective outermost barrier can become compromised, making the skin less hydrated, more fragile, and susceptible to irritation and environmental damage. In addition, men, more than women, generally prefer fewer steps and products. Accordingly, there has been and remains a need for a single men's skin care product, with clinically-demonstrated efficacy, that provides multiple benefits, including reducing the appearance of signs of aging (facial fine lines and wrinkles and skin laxity). This need is met by the present invention.

Self-foaming shaving lotions are known in the personal care arts and are described, for example, in U.S. Patent Application Publication Nos. 2003/0026775 and 2009/0142290, assigned respectively to Gillette and the Procter & Gamble Company. Neither of these references teaches or suggests use of the disclosed shaving composition reduces the appearance of aging (e.g., facial fine lines and wrinkles or skin laxity).

SUMMARY OF THE INVENTION

The present invention provides a male shaving product that allows a close comfortable shave and, with repeated use of at least two weeks, effects a reduction in fine lines and wrinkles and other signs of skin aging, including skin firmness.

The multi-functional male shaving product of the present invention includes three required components in a water-based carrier. The required components are: (i) a combination of surfactants comprising an alkyl isethionate and a glyceryl alkanoate; (ii) a copolymer of acrylamide and diallyldimethylammonium chloride; and (iii) a yeast extract, an algae extract, an extract of *Chondrus crispus*, and glucosamine hydrochloride.

The shaving product can include a continuous self-foaming agent.

DETAILED DESCRIPTION OF THE INVENTION

As used herein in connection with the shaving product of the present invention, unless otherwise noted or clear from the context, all percentages are by weight with respect to the total composition.

One skilled in the art of formulating personal care products knows that the exact composition of such formulations is subject to acceptable variation due to, for example, weighing and rounding errors. Thus, the percentages for the constituents of a particular batch or lot may not always add exactly to 100%. The percentages recited herein should be interpreted in light of this normal variation that would be expected by the skilled artisan.

The male shaving product of the present invention is a multi-functional shaving product. One function is to provide for comfortable shaving of the face and neck, without pull or dragging and the associated "razor burn".

Beyond improving the closeness and comfort of a shave, the multi-functional male shaving product of the present invention provides benefits that make the skin look younger. Upon repeated use, that is when used daily for a period of two weeks, especially four weeks, more especially twelve weeks, the shaving product of the present invention provides an anti-aging function—reducing the appearance of facial fine lines and wrinkles, and improving skin hydration, smoothness, and superficial as well as integral firmness. This anti-aging function is discussed in more detail below. The shaving product of the present invention also provides a calming, anti-inflammatory, soothing effect to the skin of the repeated user.

Additionally, the multi-functional shaving product of the present invention can be used as a gentle, non-irritating cleanser for portions of the face not having facial hair that the user desires to cut by shaving.

The multi-functional shaving product of the present invention includes, in addition to a water-based vehicle, three required components and, in particularly preferred embodiments, a fourth component. Each of these components is discussed below.

The multi-function shaving product of the present invention includes, as a first required component, a combination of an alkyl isethionate (a salt of a 2-alkanoyloxyethanesulfonic acid) and a glyceryl alkanoate (glycerine esterified with a fatty acid) surfactant.

The alkyl group of the alkyl isethionate portion of the combination of surfactants has between 8 and about 22 carbon atoms. The alkyl isethionate can be an alkyl isethionate in which all of the alkyl groups have the same number of carbon atoms, or the alkyl isethionate can be a mixture of alkyl isethionates in which all the alkyl groups do not have the same number of carbon atoms, as is common in the alkyl isethionates of commerce. Preferably, at least about 50%, by weight, of the alky isothionate used consists of alky isothionate having 12 carbon atoms (i.e. 2-dodecanoylethanesulfonic acid) or more. Jordapon® CI Prill (available from BASF) is an alkyl isothionate preferred for use in the present invention.

The alkanoate (acyl) portion of the glyceryl alkanoate portion of the combination of surfactants has between 10 and 16, preferably 12, carbon atoms. The skilled artisan knows that glyceryl alkanoate surfactants of commerce may contain a mixture of esters in which one, two, or all three alcohol groups of glycerin are esterified. Reference to glyceryl alkanoate should be understood to refer to such mixtures and materials of commerce that are such mixtures are useful in the practice of the present invention. Lexemul® T from Inolex is an example of a preferred glyceryl alkanoate for use in the present invention.

The multi-functional shaving product of the present invention includes, as a second required component, a copolymer of acrylamide and diallyldimethylammonium chloride. Polyquaternium-7 (INCI name) is preferred.

The multi-functional shaving product of the present invention further includes, as a third required component, glucosamine hydrochloride and three extracts: an extract of *Chondrus chrispus*, an extract of yeast, preferably an extract of *Saccharomyces cerevisiae*, and an extract of an algae. The shaving product of the present invention includes the extracts and glucosamine hydrochloride at a combined percentage of 6% to 10%, preferably 8%, by weight.

The multi-functional shaving product of the present invention also includes a water-based vehicle. The water-based vehicle can contain water miscible components, for example low molecular weight alcohols or diols.

The water-based vehicle can, and in preferred embodiments does, include a rheology modifier. Examples of rheology modifiers useful in the present invention include copolymers of acrylic acid and/or methacrylic acid with long-chain (e.g. $C_{10}$ to $C_{30}$) esters of acrylic acid and/or methacrylic acid; xanthans; and cellulosic polymers (e.g carboxymethyl cellulose), to mention just a few. Carbopol Ultrez® 20 (Lubrizol) is an example of a preferred rheology modifier. The kind and amount of rheology modifier are selected according to the desired viscosity and feel of the multi-functional shaving product.

Although the vehicle is water-based and includes components that are soluble in, or at least swellable by, water, the shaving product, as a whole, can contain water-immiscible components, for example alkanes, for example isohexadecane, and alkyl carbonates, for example dicapryl carbonate, to mention just two.

In particularly preferred embodiments, the multi-functional shaving product of the present invention includes 10% to 20%, preferably 15%, by weight of a continuous self-foaming agent that includes one or more low-boiling (b.p. 50° to 70° C.) partially fluorinated ethers (i.e. hydrofluoroethers), for example methyl perfluorobutyl ether and methyl perfluoroisobutyl ether.

Preferably, the low-boiling ether(s) is entrapped in small particles (nanoparticles) formed at least in part of poly(hydroxystearic acid) (CAS #27924-99-8). Upon application and during use, the low-boiling ethers are released, causing a foam to be formed. The resulting foam is described by users as being rich and easy to use, imparting cushioning and lubricity during shaving. Agents that stabilize the foam can also be included in the shaving product. PhenoMulse™ CE-1 is an example of a preferred continuous self-foaming agent useful in those embodiments of the present invention that include such a self-foaming agent.

The shaving product of the present invention can also include fragrance or tactile additives, for example essential oils from plants (leaves and fruits). Examples include essential oils from citrus fruits, spearmint, peppermint, and eucalyptus.

The shaving product of the present invention can also include one or more preservatives.

A representative non-limiting example of a multi-functional shaving product within the scope of the present invention is given in the following Table I.

TABLE I

| INCI Name | Wt. % |
|---|---|
| Water (Aqua) | QS |
| Sodium Cocoyl Isethionate | 20.00 |
| Polyhydroxystearic Acid; Isononyl Isononanoate; Ethylhexyl Isononanoate; Sodium Cocamidopropyl PG-Dimonium Chloride Phosphate; Methyl Perfluorobutyl Ether; Methyl Perfluoroisobutyl Ether; Water (Aqua) | 15.00 |
| Stearic Acid | 3.30 |
| Glyceryl Stearate SE | 3.30 |
| Dimethicone | 3.00 |
| Polyquaternium-7; Water | 3.00 |
| Cetyl Alcohol | 2.20 |
| Propanediol | 2.00 |
| Glycerin | 2.00 |
| Dicaprylyl Carbonate | 2.00 |
| Water (Aqua); Chondrus Crispus (Carrageenan) Extract | 2.00 |
| Isohexadecane | 1.50 |
| Water (Aqua); Butylene Glycol; Chondrus Crispus (Carrageenan) Extract | 1.00 |
| Preservative | 1.00 |
| Aminomethyl Propanol | 0.50 |
| Water (Aqua); Glucosamine HCl; Algae Extract; Yeast Extract; Urea | 0.50 |
| Fragrance | 0.50 |
| Acrylates/C10-30 Alkyl Acrylate Crosspolymer | 0.30 |
| Dipotassium Glycyrrhizate | 0.10 |

As discussed above, in addition to providing for a comfortable shave, repeated use of the multi-functional shaving product of the present invention provides benefits to the skin beyond cleansing and exfoliation—namely, reduction in the appearance of the visible signs of skin aging, results described in the popular vernacular as "anti-aging". By repeated use is meant daily use for at least two weeks. However, the anti-aging effects are even more apparent after 4 weeks and, especially, after 8 and especially 12 weeks of daily use.

Anti-aging effects achieved by repeated use of the multi-functional shaving product of the present invention include a reduction (33%+) in fine lines and wrinkles, measured by, for example, profilometry, and an improvement in uniformity of skin complexion (measured for example in terms of Hunter L, a, b values). Improvements in hydration and firmness are also observed. Other clinical measures demonstrating the efficacy of a skin care product in achieving so-called "anti-aging" results known in art can also be used.

As demonstrated in the following clinical study, improvements in the appearance of superficial facial fine lines and wrinkles (reduction in number, length and depth of lines and wrinkles) and increased skin firmness are observed within eight weeks or less of daily use.

The study (test) panel is composed of 25 male subjects, aged 35-55 years, evaluated at baseline and after 2, 4 and 8 weeks of daily use of the multi-functional shaving product conforming to the formulation in Table I, supra.

Inclusion criteria are:
1. Males between the ages of 35 and 55 (inclusive) in general good health (no physical required).
2. Individuals with a global fine line and wrinkle score of "5" or greater (noticeable) on the face (for qualification purposes only).
3. Individuals with a sagging facial skin score of "5" or greater (noticeable) on the face (for qualification purposes only).
4. Individuals who can read, understand and sign the Informed Consent form.
5. Individuals with anticipated ability to follow the study directions, to participate in the study, to return for all visits and to apply the product as per instructions.

Exclusion criteria are:
1. Individuals with any visible skin disease.
2. Individuals with sunburn, suntan on the face or planning a vacation with sun-exposure or planning the use of a tanning booth during the course of the study.
3. Individuals engaged in a concurrent research project of a facial product.
4. Individuals taking medications which might confound the test results including the use of steroidal/non-steroidal anti-inflammatory drugs or antihistamines.
5. Individuals who have undergone a laser resurfacing or dermabrasion procedure on the face in the past 2 years or a chemical face peel (deep peel in the past 1 year; superficial peel in the past two months).
6. Individuals with acne, active atopic dermatitis/eczema or psoriasis.
7. Individuals who have had a surgical "cosmetic" procedure on the face within the past 10 years.
8. Treatment or history of any type of cancer.
9. Individuals who are currently under treatment for asthma or diabetes.
10. Individuals with a known sensitivity to cosmetics or personal care products.

The study procedure is as follows:

Subjects report to the Testing Facility for the baseline visit. A trained technician globally evaluates fine lines and wrinkles and sagging skin on the face of each subject to determine qualification. Digital photographs are taken of the face of each subject and analyzed to determine changes (if any) in global fine lines and wrinkles. A Cutometer® (Courage+Khazaka, Germany) is used to measure skin firmness/elasticity. Subjects are required to respond to a baseline questionnaire. Evaluation criteria are listed infra.

Subjects are given the test product, use instructions, and a daily diary. Subjects are instructed to report to the Testing Facility following 2, 4 and 8 weeks of shaving product use for additional instrumental measurements and digital photographs. Additionally, at each visit, subjects are required to respond to a questionnaire. Each morning, subjects are instructed to apply the test product prior to the entire face, including the crow's feet area. (The product is designed to act as a cleanser as well as a shaving cream.) Subjects are then instructed to shave desired areas of facial hair growth and wash the foam off of the entire face. Finally, subjects are instructed not to use any new skin care products or cosmetics during the test period.

Clinical evaluation is performed according to the following evaluation criteria at baseline and after 2, 4, and 8 weeks. Evaluation for all parameters is conducted according to the scales and procedures outlined below.

At the baseline visit (for qualification only), a trained technician visually evaluates each subject for the appearance of both (i) facial fine lines and wrinkles and (ii) skin laxity (sagging) according to the scale below: 0=None; 1-3=Slight; 4-6=Noticeable; 7-9=Very Noticeable In addition, at baseline and at each visit, the elasticity/firmness of the skin is measured on the face of each subject using the Cutometer®. An increase in Cutometer® measurements indicates an improvement (increase) in skin elasticity/resiliency. A decrease represents a worsening.

At each visit, a trained technician evaluates the face of each subject for irritation according to the following scale: 0=No irritation present; +=Barely perceptible irritation present; 1=Mild irritation present; 2=Moderate irritation present; 3=Marked irritation present; 4=Severe irritation present.

At baseline and at each visit, digital images of the face of each subject are taken from the front, right and left views. In order to ensure consistency between the photographs, each subject is draped with a black cloth around the shoulders in order to eliminate the appearance of clothing in the pictures and each subject wears a black headband to pull hair off of and away from the face. The images are analyzed using Image Pro® software (MediaCybernetics, Bethesda, Md.) to determine changes in the number, length and depth of fine lines and wrinkles Finally, at each study visit, subjects respond to a self-assessment questionnaire.

All data points collected after 2, 4 and 8 weeks of the multi-functional shaving product of the present invention use are compared to the baseline of each subject for differences between the time points. Data collected from discontinued subjects may be included in the statistical analyses up to the point of discontinuation. The summation of the difference is analyzed using the Wilcoxon Signed-Rank Test. A response is considered statistically significantly different from the baseline when the p-value is s 0.05.

In certain embodiments, "anti-aging results"—reducing the appearance of one or more of the signs of skin aging (facial fine lines and wrinkles and skin laxity) according to the assessment methods described above—that are even more surprising and unexpected (e.g., in terms of rapidity with which improvements are visible) are achieved by using the multi-functional shaving cream of the present invention in further combination with a skin treatment product that contains a retinoid, preferably retinol, still more preferably retinol that is encapsulated or otherwise provided in a controlled release delivery system.

In a more preferred aspect of embodiments in which a skin treatment product that contains a retinoid, preferably retinol, is used, the skin treatment product is further comprised of at least one, preferably at least two, topical anti-inflammatory skincare agents. Preferred topical anti-inflammatory/soothing skincare agents include, but are not limited to, allantoin and/or arnica oil.

In another more preferred aspect of embodiments in which a skin treatment product that contains a retinoid, preferably retinol, is used, the skin treatment product is further comprised of at least one, preferably at least two topical moisturizing agents. Non-limiting examples of preferred topical moisturizing agents suitable for use in the skin treatment product are shea butter, aloe vera, and/or beta glucan.

In another more preferred aspect of embodiments in which a skin treatment product that contains a retinoid, preferably retinol, is used, the skin treatment product is further comprised of at least one topical anti-oxidant. A preferred topical anti-oxidant is ergothioneine.

In another more preferred aspect of embodiments in which a skin treatment product that contains a retinoid, preferably retinol, is used, the skin treatment product is further comprised of at least one short-chain acylated peptide, preferably having three to six amino acids, said peptide functioning to increase the expression of one or more genes that code for extracellular skin matrix (ECM) proteins and/or to decrease the expression of the expression of one or more genes that code enzymes that degrade ECM proteins. A non-limiting example of such a peptide is TEGO® Pep 4-17 (INCI: Tetrapeptide-21, Glycerin; Butylene Glycol; Aqua).

In an especially preferred aspect of embodiments in which a skin treatment product that contains a retinoid, preferably retinol, the retinol is encapsulated and the skin treatment product contains at least one anti-inflammatory/soothing skincare agent, at least one topical moisturizing agent, at least one topical anti-oxidant, and at least one short-chain acylated peptide.

We claim:

1. A multi-functional, foaming male shaving product comprising:
   i) a surfactant blend consisting of an alkyl isethionate and a glyceryl alkanoate, wherein the ratio, by weight of alkyl isethionate to glyceryl alkanoate is between 5:1 to 8:1,
   ii) a copolymer of acrylamide and diallyldimethylammonium chloride;
   iii) a combination of a yeast extract, an algae extract, an extract of *Chondrus crispus*, and glucosamine hydrochloride; and
   iv) a continuous self-foaming agent containing a volatile hydrofluoroether.

2. The multi-functional, foaming male shaving product of claim 1 wherein the alkyl isethionate and the glyceryl alkanoate are present at a combined concentration of 15% to 25%, by weight.

3. The multi-functional, foaming male shaving product of claim 1 wherein the copolymer of acrylamide and diallyldimethylammonium chloride is present at a concentration of 1% to 2% by weight, of the multi-functional male shaving product.

4. The multi-functional male shaving product of claim 1 wherein the continuous self-foaming agent containing a volatile hydrofluoroether is present at 10% to 20% by weight.

5. The multi-functional, foaming male shaving product of claim 1 wherein the alkyl isethionate is sodium cocoyl isethionate.

6. The multi-functional, foaming male shaving product of claim 1 wherein the glyceryl alkanoate is glyceryl stearate.

7. The multi-functional, foaming male shaving product of claim 1 wherein the volatile hydrofluoroether is selected from the group consisting of methyl perfluorbutyl ether and methyl perfluoroisobutyl ether.

* * * * *